United States Patent [19]

Kolff

[11] Patent Number: 4,510,628
[45] Date of Patent: Apr. 16, 1985

[54] ARTIFICIAL HEART VALVE MADE BY VACUUM FORMING TECHNIQUE

[75] Inventor: Willem J. Kolff, Salt Lake City, Utah

[73] Assignee: University of Utah, Salt Lake City, Utah

[21] Appl. No.: 374,051

[22] Filed: May 13, 1982

[51] Int. Cl.$^3$ .............................................. A61F 1/00
[52] U.S. Cl. ................................................... 3/1.5
[58] Field of Search .......................... 3/1.5; 156/242; 137/525.1, 525.3; 29/458

[56] References Cited

U.S. PATENT DOCUMENTS

| | | | |
|---|---|---|---|
| 3,320,972 | 5/1967 | High et al. | 137/525.1 |
| 3,445,916 | 5/1969 | Schulte | 29/458 |
| 3,589,392 | 6/1971 | Meyer | 137/525.1 |
| 3,608,097 | 9/1971 | Bellhouse et al. | 3/1 |
| 3,717,883 | 2/1973 | Mosher | 3/1.5 |
| 3,736,598 | 6/1973 | Bellhouse et al. | 3/1 |
| 3,744,060 | 7/1973 | Bellhouse et al. | 3/1 |
| 3,744,062 | 7/1973 | Parsonnet | 3/1 |
| 3,755,823 | 9/1973 | Hancock | 3/1 |
| 3,861,416 | 1/1975 | Wichterle | 137/525.3 |
| 3,966,401 | 6/1976 | Hancock et al. | 8/94.11 |
| 4,218,783 | 8/1980 | Reul et al. | 3/1.5 |
| 4,222,126 | 9/1980 | Boretos et al. | 3/1.5 |
| 4,265,694 | 5/1981 | Boretos et al. | 156/242 |
| 4,291,420 | 9/1981 | Reul | 3/1.5 |
| 4,364,126 | 12/1982 | Rosen et al. | 3/1.5 |
| 4,364,127 | 12/1982 | Pierce et al. | 3/1.5 |

OTHER PUBLICATIONS

Russell, F. B., D. M. Lederman, P. I. Singh, R. D. Cumming, R. A. Morgan, F. H. Levine, W. G. Austen and M. J. Buckley, "Development of Seamless Tri-leaflet Valves", Trans. Am. Soc. of Artif. Intern. Organs, vol. 26, pp. 66–71, 1980.

Wiseman, C. B., W. S. Pierce, J. H. Donachy, W. E. Pae, J. L. Meyers and G. A. Prophet, "Polyurethane Trileaflet Cardiac Valve Prothesis: In Vitro and In Vivo Studies", Trans. Am. Soc. of Artif. Intern. Organs, vol. 28, pp. 167–168, 1982.

Kiraly, R., R. Yozu, D. Hillegass, H. Harasaki, S. Murabayashi, J. Snow and Y. Nose, "Hexsyn Trileaflet Valve: Application to Temporary Blood Pumps", Artifical Organs, vol. 6, No. 2, pp. 190–197, 1982.

Husnegel, C. A., and P. W. Conrad, "A New Approach to Aortic Valve Replacement", Annals of Surgery, vol. 167, pp. 791–795, 1968.

Roe, Benson B., "Late Followup Studies on Flexible Leaflet Prosthetic Valves", Journal of Thoracic and Cardiovascular Surgery, vol. 58, pp. 59–61, 1969.

Mohri, H., E. A. Hessel, II, R. J. Nelson, H. N. Anderson, D. H. Dillard, and K. A. Merendino, "Design and Durability Test of Silastic Trileaflet Aortic Valve Prostheses", Journal of Thoracic and Cardiovascular Surgery, vol. 65, pp. 576–582, 1973.

Akutzu, T., B. Dreyer and W. J. Kolff, "Polyurethane Heart Valves in Animals", *Journal of Applied Physiology*, vol. 14, 1959, pp. 1045–1048.

(List continued on next page.)

*Primary Examiner*—Richard J. Apley
*Assistant Examiner*—David J. Isabella
*Attorney, Agent, or Firm*—Workman, Nydegger & Jensen

[57] ABSTRACT

An artifical heart valve having thin, seamless leaflets which converge to the center of a frame from the frame's inner wall. The leaflets each have a convex outflow surface and a concave inflow surface. The leaflets meet along adjacent edges to form cusps. Sinus valsalvae sections of the valve are formed as rounded recesses defined in the valve frame's inner wall as continuous curved profiles of the respective leaflet concave surfaces. The valve is fabricated by vacuum molding techniques whereby layers of elastomer are vacuum formed to comprise the leaflet and sinus valsalvae portions. In one embodiment, the leaflets are all formed from two or more layers of elastomer which are cut to define the leaflet edges or commissures. One elastomer layer extends along the frame recess to provide continuity for each leaflet and its valsalvae. The resulting structure has no rims or seams in the inflow or outflow paths.

13 Claims, 19 Drawing Figures

OTHER PUBLICATIONS

Akutzu, T., V. Mirkovitch and W. J. Kolff, "Teflon as Experimental Replacement for Mitral and Tricuspid Valves", *Journal of Surgical Research,* vol. 1, pp. 188–191, 1961.

Hessel, E. A., K. J. May, Jr., G. P. Steinmetz, Jr., H. N. Anderson, D. H. Dillard, and K. A. Merendino, "A Prefabricated Semirigid Tricuspid Aortic Valve Prosthesis", *Journal of Thoracic and Cardiovascular Surgery, vol. 54, pp. 227–245, 1967.*

G. E. Chetta and J. R. Lloyd, "The Design, Fabrication and Evaluation of a Trileaflett Prosthetic Heart Valve", Journal of Biomechanical Engineering, vol. 102, pp. 34–41, 1980.

Notice of Issuance of U.S. Pat. No. 4,364,126 (Rosen et al.) from the United States Patent and Trademark Office Official Gazette dated Dec. 21, 1982.

Notice of Issuance of U.S. Pat. No. 4,364,127 (Pierce et al.) from the United States Patent and Trademark Office Official Gazette dated Dec. 21, 1982.

U.S. Patent  Apr. 16, 1985  Sheet 1 of 2  4,510,628
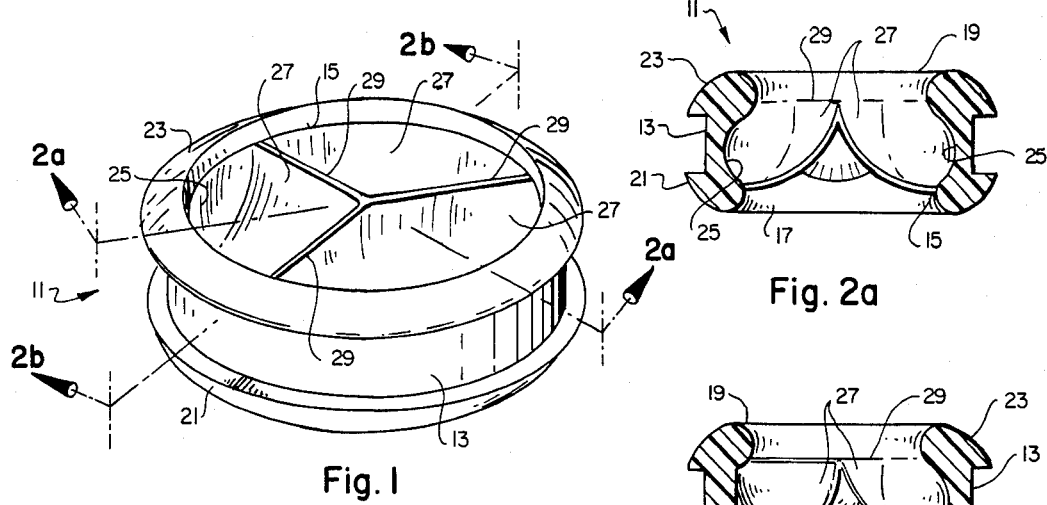
Fig. 1
Fig. 2a
Fig. 2b
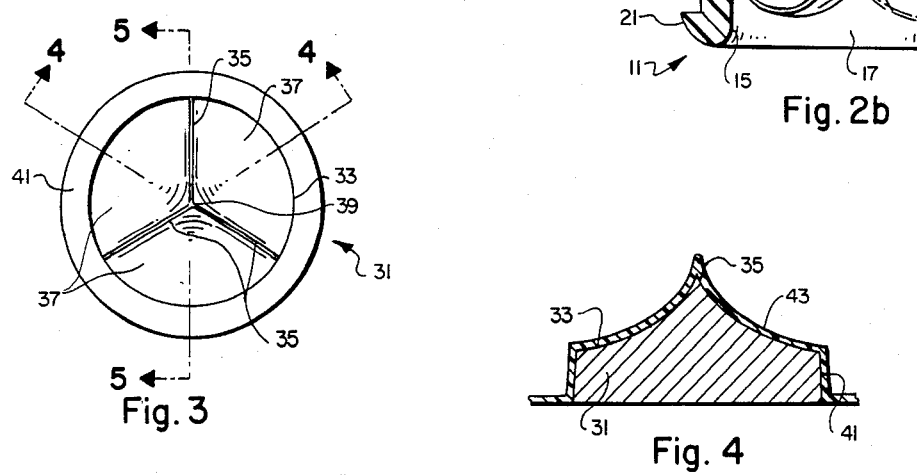
Fig. 3
Fig. 4
Fig. 5
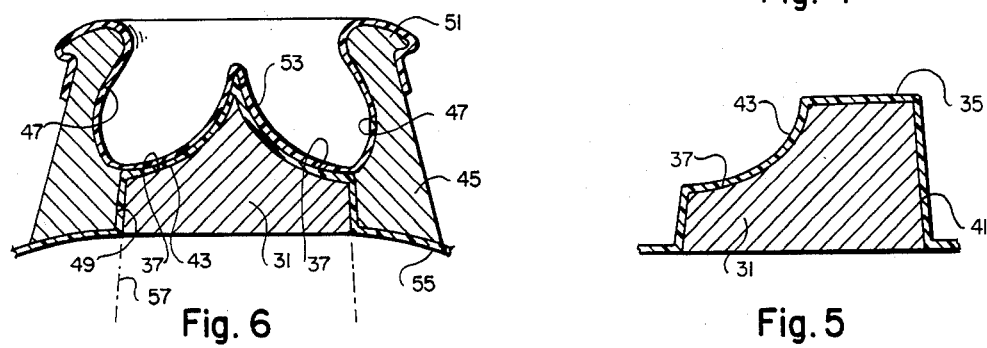
Fig. 6
Fig. 7
Fig. 8

ARTIFICIAL HEART VALVE MADE BY VACUUM FORMING TECHNIQUE

BACKGROUND OF THE INVENTION

1. Field of the Invention

The present invention relates to artificial heart valves and, more particularly, to an improved artificial heart valve made by a vacuum forming technique.

2. The Prior Art

There have been many artificial heart valves developed over the years but none has proved entirely satisfactory. Mechanical valves, such as ball valves, disc valves, hinged valves, etc., are subject to wear and tear and ultimate failure; in addition, in some cases their physical parameters, such as size, shape, flow characteristics, etc., prove unsatisfactory for long term use in the intended environment.

Leaflet valves have appeared to present much promise to prior art experimenters, primarily because leaflet valves closely resemble the actual valving mechanism in natural heart valves. Leaflet valves include flaps or leaflets which project from a frame to cover the framed area. Flow through the frame in one direction causes the leaflets to freely flex downstream to permit through flow. Flow in the opposite direction is resisted by the leaflets.

To my knowledge, the only leaflet-type artificial heart valves which are commercially available have leaflets made from a material which is of human or animal origin. Examples of these are porcine valves, dura mater valves, fascia lata valves and pericardial valves. Such valves cannot be manufactured on a large scale, both because of limitations on available material, in some cases, and primarily because there are no known mass production techniques which function with animal tissue material.

There have been many experiments conducted with artificial heart leaflet valves made of synthetic material such as Teflon, Dacron and Gore-Tex, none of which have led to a satisfactory result. In addition, there have been attempts at the U.S. National Institute of Health to fabricate leaflet valves by injection molding techniques; this, too, was not satisfactory.

Recently, there has been a report by the Avco-Everett Research Labs entitled "Development of an Electrohydraulic Left Heart System" by Sing et al, May 1981. In this report a tricusp semilunar valve is disclosed as being made by solution casting over a male mold. The leaflets are separated by cutting with a Teflon coated knife. The entire structure is later glued with a polyurethane solution over a smooth mandrel to a blood pump structure on one side or to an outflow tube on the other side. This process is extremely cumbersome.

SUMMARY AND OBJECTS OF THE INVENTION

It is a primary object of the present invention to provide an artificial heart valve made of synthetic material which operates reliably and efficiently in a manner closely resembling that of natural heart valves.

It is another object of the present invention to provide an artificial heart valve made of synthetic material which is reliable and which can be readily mass produced.

It is still another object of the present invention to provide a method of fabricating artificial heart valves inexpensively, rapidly and simply.

In accordance with the present invention, an artificial heart valve is fabricated by a vacuum molding process which uses pre-fabricated sheets of thermoplastic elastomers. In one presently preferred embodiment of the invention, a tricusp semilunar heart valve is formed by this process in a shape roughly patterned after nature's design for human and animal aortic and pulmonary artery valves. The valve frame is preferably annular and has three leaflets projecting radially inward therefrom to converge at the substantial center of the framed area. The leaflets are contoured to present a convex face upstream and a concave face downstream. Adjacent edges of the leaflets meet, when the leaflets are unflexed by flow, in three radially-extending and downstream-projecting cusps. The inner wall of the frame is provided with three rounded recesses, each comprising a curved extension of the concave surface of a respective leaflet. These recesses, extending downstream of the leaflets, simulate the sinus valsalvae of human and animal heart valves. The valve frame outer wall is provided with a quick-disconnect fitting for attachment to an artificial aorta, blood pump, or the like.

The valve can be fabricated as an integral part of a tube or a pump or it can be fabricated within a separate ring adapted for connection to a flow tube. Fabrication of an aortic valve employs a male mold having its upper surface contoured to present three upwardly-facing and radially-extending cusps which separate three curved recesses in the mold. A sheet of thermoplastic elastomer is heated and drawn by vacuum over the exposed upper surface of the mold. A short annular mold, which may constitute the frame of the final valve, is placed concentrically about the elastomer-covered male mold. The annular mold is roundedly recessed to form three extensions of the three curved recesses in the male mold, thereby defining the sinus valsalvae portions of the mold. Another layer of elastomer is then heated and vacuum-drawn over the exposed upper side of the annular mold and elastomer-covered surfaces of the male mold. The male mold can then be removed and the leaflets cut along their edges formed at the cusps of the male mold. The resulting valve presents no seams or rims in the blood flow path since the only transition between the two molded elastomer layers is at the leaflet edges. A similar technique is employed to fabricate an artificial mitral valve on a female mold.

These and other objects and features of the present invention will become more fully apparent from the following description and appended claims taken in conjunction with the accompanying drawings.

BRIEF DESCRIPTION OF THE DRAWINGS

FIG. 1 is a view in perspective of one presently preferred embodiment of an artificial heart valve constructed in accordance with the principles of the present invention;

FIG. 2a is a view in section taken along lines 2a—2a of FIG. 1;

FIG. 2b is a view in section taken along lines 2b—2b of FIG. 1;

FIG. 3 is a top view in plan of a male mold employed to fabricate an aortic valve in accordance with one fabrication method of the present invention;

FIG. 4 is a view in section taken along lines 4—4 of FIG. 3 and showing one layer of material vacuum formed on the male mold;

FIG. 5 is a view in section taken along lines 5—5 of FIG. 3 and showing one layer of material vacuum formed on the male mold;

FIG. 6 is a view in section, similar to FIG. 4, but with an annular mold and second vacuum formed layer added;

FIG. 7 is a view in section, similar to FIG. 5, but with the annular mold and second vacuum formed layer added;

FIG. 8 is a top view in plan of a female mold employed to fabricate a mitral valve in accordance with another aspect of the present invention;

DETAILED DESCRIPTION OF THE PREFERRED EMBODIMENTS

Figure 9:
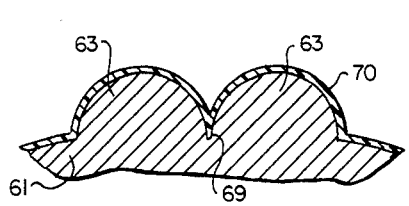
FIG. 9 is a view in section taken along lines 9—9 of FIG. 8 and showing one layer of material vacuum formed on the female mold.

Reference is now made to the accompanying drawings wherein like parts are designated with like numerals throughout.

Referring specifically to FIGS. 1, 2a and 2b, one presently preferred embodiment of the present invention includes an annular frame defined by a ring 11 having a diameter which is considerably larger than its axial length. The ring 11 has an outer wall 13 and an inner wall 15. Opposite longitudinal ends of the ring 11 (see FIGS. 2a and 2b) are designated inflow end 17 and outflow end 19 to characterize the direction of axial flow through the valve. Each of the ends 17 and 19 have annular lips 21 and 23, respectively, projecting radially outward from outer wall 13. Lips 21 and 23 serve to provide snap-on connection means for connecting the valve to suitably contoured artificial aorta, atria and ventricles. The inner wall 15 of the ring is provided with three rounded recesses 25, each of which extends angularly for approximately 120°, as hereinafter more fully described.

Three seamless, flexible, membrane-like leaflet members 27 project from inner wall 15 to the radial center of ring 11. Each leaflet has a pair of edges 29 (see FIG. 1) which converge to the center of the ring. A slit is provided between the edges 29 of adjacent leaflets. The slit or opening closes immediately so as to provide a seal against back flow through the ring 11 when the leaflets are unflexed. Each of the leaflets 27 is curved so as to prevent a concave surface facing downstream and a convex surface facing upstream. The recesses 25 (see FIGS. 2a and 2b) each form a continuous curved profile with a respective concave surface of a leaflet 27, the profile extending from the leaflet edges upstream along the concave surface of the leaflet 27 and then back downstream along its convex surface. The adjacent pairs of edges 29 of leaflets 27 form three cusps which may reside in a common plane. In the embodiment of FIG. 1, the plane of the cusps is situated just below the outlet lip 23, as shown best in FIGS. 2a and 2b. It will be understood that the leaflets 27 need not necessarily converge in a plane, so long as the adjacent edges 29 meet in the closed position.

The valve of the present invention can also be constructed with two leaflets, to form a bi-cusp embodiment, ow with one leaflet, to form a mono-cusp embodiment as illustrated and described in my copending patent application, Ser. No. 298,420, filed Sept. 1, 1981, and incorporated herein by reference.

Flow under pressure, which originates through the inlet end 17 of the valve, impinges upon the convex surfaces of leaflets 27, forcing them to flex in a downstream direction. The flexed leaflets separate at their adjacent edges 29 to permit flow to pass therethrough. The greater the dynamic pressure of the flowing fluid, the greater will be the downstream flexure of leaflets 27 and, therefore, the greater will be the flow opening through the valve.

As flow proceeds in a downstream direction through the valve it creates a low pressure region in the concave surfaces of leaflets 27 by aspirating fluid therefrom. This low pressure region causes a portion of the flow periphery to be drawn off into a vortical-like flow around the continuous curved profile comprising recesses 25 and the concave surfaces of leaflets 27. More specifically, this secondary or vortical flow leaves the periphery of the flowing fluid proximate the downstream lip 23, from whence it flows back upstream along the recesses 25. Upon reaching the leaflets 27 the secondary flow is re-directed back upstream to join the main flow through the valve. The recesses 25 thus simulate the sinus valsalvae in human and animal heart valves, using the secondary flow to wash out any blood which might coagulate and collect on the concave leaflet surface. In addition, as in the natural sinus valsalvae, the secondary flow helps to close the leaflets as the flow through the valve terminates.

The valve of FIG. 1 is constructed with a ring 11 which is separate from but readily connected to other components such as an artificial aorta, atrium or ventricle. However, it should also be noted that the valve can be constructed as an integral part of such components, as further described herein below.

When blood flows through a valve, it should ideally never meet a rim or seam in either the inflow or outflow tract where different sheets or layers of material are joined. Such seams tend to be collection points for coagulation and eventual blockage of flow through the valve. The present invention includes methods for fabricating the valves of the present invention, which methods assure that no such seams are provided in the flow path. These methods are described in detail in the following paragraphs.

The artificial heart valve of the present invention may be constructed using a novel vacuum-molding process that is simple, fast and inexpensive. By way of background, vacuum-molding involves a process in which a sheet or layer of thermoplastic polymer or elastomer material is heated until it becomes very soft and malleable. The soft layer of thermoplastic is then lowered over a mold and a vacuum is created under the mold which sucks the elastomer tightly over the top of the mold. In this way, the thermoplastic material is formed by the mold. Mechanical help, for example by pressing the top of the vacuum-formed thermoplastic layer with a wooden form, may be used to smooth the vacuum-formed layer of thermoplastic and this is sometimes advantageous.

Using this technique, a vacuum formed print made over a convex mold will have an exact inner dimension. A vacuum formed print made over a concave mold will have an exact outer dimension. Thus, one can predict an exact fit between the prints vacuum formed over convex and concave molds when the molds themselves are fitted, which can easily be done by casting one mold inside the other.

FIGS. 3–7 relate to one presently preferred method for fabricating an artificial heart outflow valve, commonly referred to as the aortic valve, which is situated between the artificial ventricle and aorta and which controls the flow of blood out of the ventricle and into the aorta.

Referring specifically to FIG. 3, a male mold 31 has a top surface 33 contoured to correspond to the convex inlet side of the valve of FIG. 1. In other words, the upward-facing surface 33 of mold 31 includes three co-planar cusps 35 pointing upward and extending radially outward from a common point 39. The spaces 37 between the cusps 35 are concave, identical in curvature to the convex inlet surfaces of leaflets 27 in FIG. 1. The upper surface 33 of the mold is raised from the mold base (see also FIG. 4) by a frusto-conical platform 41 which tapers upwards at a small angle on the order of three degrees. The frusto conical platform 41 has been enlarged in FIG. 3 for purposes of illustration.

Referring to FIGS. 4 and 5, in forming the valve, a first layer 43 of elastomer is vacuum molded over the top surface 33 and platform 41 of mold 31. Next, as illustrated in FIGS. 6 and 7, an axially short annular mold 45 is placed concentrically about and in adjacent relationship with mold 31. The lower part of the inner surface 49 of annular mold 45 is contoured to match the platform 41 of mold 31. The recesses 47 of annular mold 45 extend as a continuation of respective recesses 37 in mold 31. Thus, the curved concave surfaces 47 of mold 45 correspond to the sinus valsalvae portions of the valve. Annular mold 45 may include, as an option, an annular lip 51 at its outlet end which serves to form a quick disconnect or snap coupling to permit connection to an artificial aorta. A second layer of elastomer 53 (see FIGS. 6 and 7) is vacuum formed over mold 45 and the exposed portion of layer 43 residing on top surface 33 of mold 31. For this purpose, air spaces or grooves (not shown) should be provided on the inside of the annular mold 45 between the bottom of recesses 47 and its base so that air can be evacuated during the vacuum forming process.

After removal of mold 31, the valve leaflets are cut where they are joined, either with a knife or with a special cutting tool having basically the same shape as surface 33 of mold 31 but with a very sharp cutting edge at the cusps.

The valve fabricated in accordance with the steps described above can be fused to the inside of a ring 11 (see e.g., FIGS. 1–2) if the ring is made of the proper complementary polymer or elastomer. The ring can then be quickly connected, as described earlier, to an artificial ventricle at the inflow side or to an artiificial aorta at the outflow side. "Quick connects" are rings with an inside ridge that fits over the corresponding lips 21 or 23 of ring 11. Such rings may be part of an artificial aorta, as assumed above, or of either the artificial atrium or an artificial ventricle. Alternatively, if the valve is not fused to a ring, it can be bonded directly to an artificial ventricle or an artificial aorta. For example, the valve can be cut at lip 51 and glued directly to the aorta using an elastomer solution. The base 55 (see FIGS. 6 and 7) can be the wall of a pump or artificial ventricle, or, as illustrated in phantom lines 57, the wall of a tube. The valve can thus serve as an outflow valve directly connected to the ventricle wall and forming an integral part of that wall.

It will be noted that the only transition between layers 43 and 53 in the flow path is at the cut edges of the leaflets. This transition is not directly in the flow path and extends over a thin line so as to minimize any area where blood can collect and coagulate.

The valve of the present invention may also be formed as an inflow valve, commonly referred to as a mitral valve. The inflow section is called the artificial atrium. One presently preferred method for forming this valve embodiment is illustrated in FIGS. 8–13.

Referring specifically to FIG. 8, a female mold 61 includes three dome-like convex projections 63. These projections 63 provide the mold surfaces for both the valve leaflets and the sinus valsalvae recesses. The dashed line 65 in FIG. 8 represents the demarcation border between the leaflets and sinus valsalvae. The projections are spaced from one another by channels 67 which extend radially outward from a common point 69. These channels 67 are just wide enough to permit a heated elastomeric membrane to be drawn into them during a vacuum-forming process. The base of mold 61 may be a cylinder or part of the mold for a pump or ventricle. The cylinder or ventricular pump mold should preferably be either made of porous material or provided with multiple small holes to permit proper vacuum-forming.

Figure 10:
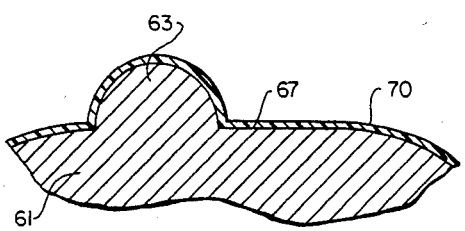
FIG. 10 is a view in section taken along lines 10—10 of FIG. 8 and showing one layer of material vacuum formed on the female mole.
Figure 11:
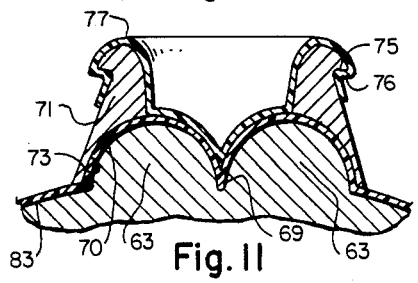
FIG. 11 is a view in section, similar to FIG. 9, but with an annular mold and second vacuum formed layer added.
Figure 12:
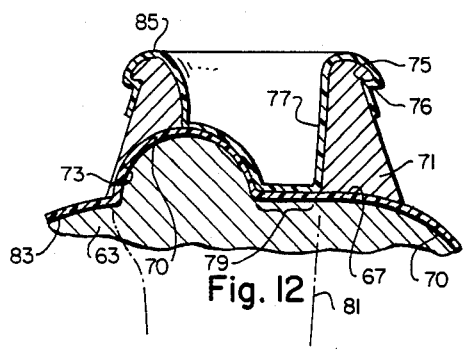
FIG. 12 is a view in section, similar to FIG. 10, but with the annular mold and second vacuum formed layer added.
Figure 13:
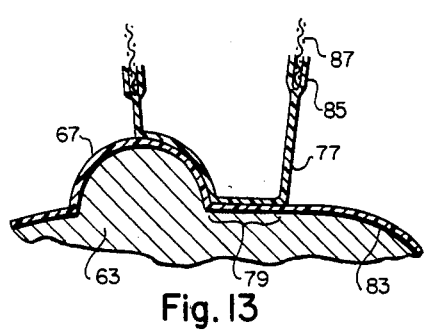
FIG. 13 is a view in section, similar to FIG. 10, but with an artificial atrium added.

Referring to FIGS. 9 and 10, an elastomeric membrane 70 is vacuum-formed over mold 61. Next, an annular mold 71, illustrated in FIGS. 11 and 12, is placed on top of the mold 61 and elastomeric layer 70. Annular mold 71 has concave inner contours 73 which fit over those portions of projections 63 which correspond to the sinus valsalvae. The mold 71 is provided with a radially-projecting lip 75 at its distal end from the mold, the lip 75 being provided with a rearwardly-formed annular groove 76 for purposes of "quick-connect" as described above.

A second elastomer layer 77 is now vacuum formed over the exposed portion of first layer 70, the exposed portion of the inner wall of annular mold 71 and lip 75. The exposed portion of first layer 70 includes only those portions corresponding to the valve leaflets since the concave inner contours 73 of ring 71 cover the sinus valsalvae section. For purposes of vacuum forming second layer 77, slits or small holes should be provided in the bottom part of annular mold 71 to permit proper evacuation, an expedient which is well known in the vacuum molding art. Likewise, three slits should also be provided in first layer 70 to provide communication with the base of mold 61. These three slits should be located along the respective cusp portions in the region designated by the reference numeral 79 in FIG. 12.

If desired, a porous cover (not shown) can be provided at the base of annular mold 71 so as to cover the portion of membrane 70 which extends along the mold at 83.

As previously noted, the base of mold 61 can either be cylindrical, as indicated by the dashed lines at 81 in FIG. 12, to form a tube, or it can be part of a ventricle or pump as generally indicated at 83. This affects formation of first layer 70 but not second layer 77.

After second layer 77 is formed, the leaflets are cut along the cusps 79 to form the finished valve. The elastomer layer 77 can be fused against ring 71, when the ring is made of suitably bondable material. If the ring is not of suitably bondable material, the elastomer can be cut around the rim 85 of lip 75 and the valve then glued directly to an artificial atrium 87 (see FIG. 13) without using the quick connect feature. The artificial atrium 87 can be made of Dacron felt or Gore-Tex.

The method described with respect to FIGS. 8–13 provides for manufacturing an inflow valve by vacuum-forming such that the valve may be directly connected to the ventricle. As a result, there is a minimum of wasted space.

FIGS. 14–18 illustrate yet another embodiment of the method of the present invention which may be used to fabricate valves which are formed on a separate ring, as previously illustrated and described in FIGS. 1–3. The valve of FIG. 1 is formed using a separate ring 11 which is not part of the structure of a flow tube, pump, ventricle, etc. Such a valve can be inserted, at one end, in many kinds of pumps or artificial hearts. The other end of the valve can be connected to either artificial atria or artificial aortas. This embodiment of the valve could also be sutured in a natural heart as a valve prosthesis, in which case the axial length of the ring can be reduced, leaving only stents where the leaflets meet along the inner wall of the ring.

Figure 14:
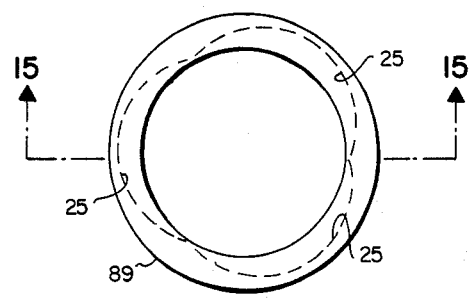
FIG. 14 is a top view in plan of another mold in the form of a ring employed in fabricating another valve embodiment of the present invention.
Figure 15:
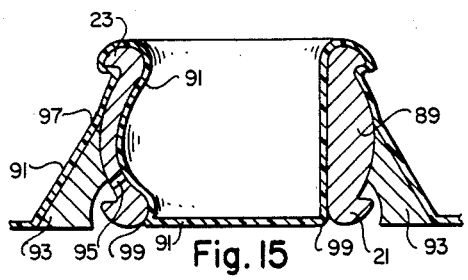
FIG. 15 is a view in section taken along lines 15—15 of FIG. 14 but showing a first layer vacuum formed thereon.
Figure 16:
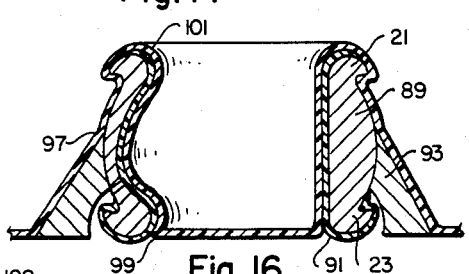
FIG. 16 is a view in section, similar to FIG. 15, but with the mold turned over and a second vacuum formed layer added.

Referring specifically to FIGS. 14 and 15, a ring 89, similar to ring 11 of FIG. 1, may be made of polymer or elastomer or, alternatively of a variety of other bondable materials. Ring 89 includes three recesses 25, corresponding to the sinus valsalvae recesses 25 in ring 11 of FIG. 1. In addition, ring 89 is provided with lips 21 and 23 for quick-connect purposes. When ring 89 is made of a proper elastomer or polymer or other suitably bondable material, the leaflets can be bonded directly to the ring during the vacuum molding process, as further described below.

As illustrated in FIG. 15, a first layer of elastomer 91 is vacuum formed on ring 89 from above. The lower part of the outer surface of ring 89 is covered by a protective ring 93 to prevent layer 91 from contacting and bonding to that part of ring 89. Protective ring 93 is positioned to permit air from above to escape between it and ring 89 during the vacuum forming process. Small holes 95 may be defined in ring 89 in the recesses 25 to permit air to escape from the area. The elastomer layer 91 is then cut annularly at 97 along the outer wall of ring 89 above protective ring 93. In addition, layer 91 is cut annularly, at 99, along the bottom edge of the inner wall of ring 89 to remove the circular portion of layer 91 at the ring's bottom. Ring 89 is then inverted (see FIG. 16), with lip 21 facing up, and a second layer 101 is vacuum formed in the same manner, using protective ring 93 to protect the other end of the outer wall of ring 89. Cuts are again made at locations 97 and 99, resulting in layer 101 remaining bonded to layer 91. The first layer 91 is preferably sprayed with glue (such as a solution of the same elastomer in a solvent) before second layer 101 is formed, thereby assuring fusing of the two layers. After the cutting of layer 101, the ring 89 is turned right side up again to the position illustrated in FIG. 17.

Figure 17:
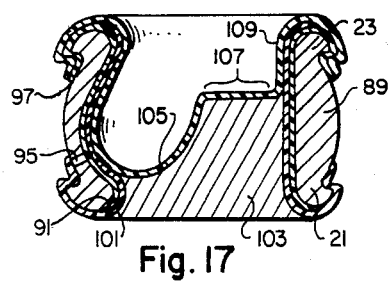
FIG. 17 is a view in section similar to FIG. 15 but showing an addition a male mold placed inside the ring, and a third vacuum formed layer added.

As illustrated in FIG. 17, the ring 89, now coated with elastomer layers 99 and 101, receives a male mold 103 concentrically therein. Mold 103 is configured to match the tricusped leaflet configuration of leaflets 27 and their edges 29 of FIG. 1, there being one leaflet recess 105 and one edge of cusp 107 on the mold illustrated in FIG. 17. A third layer of elastomer 109 is then vacuum formed over the exposed portions of layers 91 and 101 and the surface of mold 103. The thickness of layer 109 can vary over a range from five to forty thousandths of an inch. It may be advisable, during forming of layer 109, to protect the outside of ring 89 with protective ring 93 of FIG. 16. Also, in order to assume proper vacuum forming of layer 109, the holes formed in recesses 25 of ring 89 should be opened by providing very small corresponding holes in layers 91 and 101. When either the ring or the membrane layer 109 is sprayed with glue before forming, fusion is assured between the valve leaflet and ring during this vacuum forming step.

Figure 18:
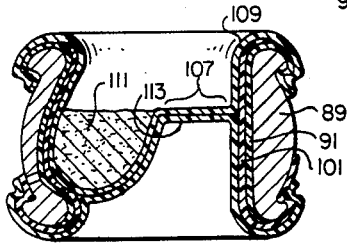
FIG. 18 is a view similar to FIG. 17 illustrating the next steps in the fabrication procedure.

The structure of FIG. 17, with mold 103 removed, can be used as a finished valve. Under such circumstances the commissures of the leaflets can be cut as described above and the valve can be employed with the single layer 109 comprising the leaflets. However, a second leaflet layer may be provided, if desired. Formation of the second layer proceeds as illustrated in FIG. 18. Specifically, after providing small slits in the commissures to assure a proper air path, a porous material 111, such as plaster of Paris, is placed in the lobes made up of the concave leaflet surfaces and recesses for the sinus valsalvae. The structure is then inverted and a second layer 113 of elastomer is vacuum formed over what was the bottom surface of layer 109. The slits made in the commissures, and the porous material 111 in the lobes, permits flow of air during vacuum forming. When the layer 113 has been formed the unit is turned right side up, and the commissures are cut at the cusps 107 in the manner described above.

The result of this vacuum forming technique is a valve that has no rims or seams in either the inflow or the outflow path of the blood since the only place where the leaflets meet is the place where the commissures are cut. It should be noted, as mentioned throughout, that fusion or bonding between adjacent vacuum formed layers, in all embodiments, can be assured by spraying one or both mating surfaces, before vacuum forming, with a glue made of the same elastomer material as the layer.

It will be appreciated that the thickness of the layers of thermoplastic polymer used for the ring 89 and the leaflets 27 are a matter of design choice. It is desirable that the ring 89 be thick enough to adequately support the leaflets, whereas the leaflets 27 must be very thin and membranous so that they can be easily flexed for purposes of the operation of the valve.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. An aritifical heart valve comprising means for forming an annular frame which defines an inflow end and an outflow end of said heart valve, and a plurality of thin leaflet members supported by said frame such that adjacent edges of each said leaflet member project radially inward toward the center of said frame to form a narrow slit between each leaflet pair through which blood flows from said inflow end to said outflow end, each leaflet member comprising a first discrete sheet of elastomeric material and a second discrete sheet of elastomeric material formed over said first sheet such that the only seam between said first and second sheets which occurs in the path of the blood as it flows from said inflow end to said outflow end occurs at said slits formed between each leaflet pair.

2. An artificial heart valve as defined in claim 1 said elastomeric sheets are bonded together.

3. An artifical heart valve as defined in claim 1 wherein each said leaflet member comprises a convex inflow surface and a concave outflow surface.

4. An artificial heart valve as defined in claim 3 wherein said annular frame comprises a ring member constructed of elastomeric material, said ring member being bonded to each said leaflet member.

5. An artifical heart valve as defined in claim 4 wherein said ring member has annular lips at said inflow and outflow ends to permit quick coupling to other artificial organs or tubes.

6. An artificial heart valve as defined in claim 4 wherein said ring member has an inner and an outer wall, and wherein the inner wall comprises a plurality of curved recesses each of which form an extension with said concave surface of one of the leaflet members.

7. An artificial heart valve comprising:
a ring member;
a plurality of thin leaflet members supported by said ring member such that adjacent edges of each said leaflet member project radially inward toward the center of said ring member to form a narrow slit between each leaflet pair, each leaflet member having an inflow surface and an outflow surface comprised of at least two thin, discrete sheets of elastomeric material bonded together so as to form discrete layers, and each leaflet member presenting a seamless, continuously curved profile at both the inflow and outflow surfaces thereof; and
said ring member being constructed of elastomeric material and being bonded to each said leaflet member, and said ring member having an inner surface which comprises a plurality of curved recesses each of which form a continuous extension of the curved profile of one of said leaflet members.

8. An Artificial heart valve comprising:
a ring member having radially inner and outer walls, and having an inlet end and an outlet end, each said end comprising means for forming a snap connection between the inflow and outflow ends of said ring member and other artificial organs or tubes connected to said ring member at the inflow and outflow ends thereof;
three flexible elastomeric leaflet members extending from respective adjacent locations disposed angularly about said inner wall, said leaflet members each having two edges which converge from said inner wall to a common point located substantially at the radial center of said annular member, each leaflet member, when unflexed, having its edges in contact with an edge of an adjacent leaflet member, each leaflet member having a curvature such that a concave surface of the leaflet member faces downstream toward said outlet end and the convex surface that faces upstream toward said inlet end; and
wherein said inner wall of said annular member is provided with rounded recesses, each recess forming a continuous curved profile with the concave surface of a respective leaflet member.

9. The valve according to claim 8 wherein each of said leaflet members comprises at least two discrete sheets of elastomeric material bonded together such that the only seam between said sheets which occurs in the path of blood flowing from said inlet end to said outlet end occurs at said edges which converge to said common point.

10. The valve according to claims 8 wherein said adjacent edges of said leaflet members are disposed substantially co-planar when said leaflet members are unflexed.

11. The valve according to claim 8 wherein said means for forming said snap connection at the inflow and outflow ends of said ring member comprises an annular lip at each said inflow and outflow end projecting radially outward for providing a snap-fit connection with other artificial organs or tubes.

12. An artificial heart valve comprising:
a ring member surrounding an area through which fluid flow is to be controlled, said ring member having an upstream side and a downstream side and inner and outer walls, said outer wall comprising an annular lip on the upstream and downstream sides thereof for providing a snap-connection to other artificial organs or tubes;
at least three thin, flexible elastomeric leaflet members extending from said inner wall to cover the surrounded area of said frame when unflexed, each leaflet member having a pair of edges, a concave surface facing downstream and a convex surface facing upstream;
at least three rounded recesses defined in said inner wall of said ring member, one recess for each leaflet member, each recess forming an extension of a continuous curved profile with the concave surface of a respective leaflet member; and
cusp means formed by adjacent edges of adjacent leaflet members for directing upstream flow around said continuous curved profiles and back downstream.

13. The valve according to claim 12 wherein each said leaflet member comprises at least two discrete sheets of thin elastomeric material bonded to one another such that the only seam between sheets occurs at said edges.

* * * * *

UNITED STATES PATENT AND TRADEMARK OFFICE
CERTIFICATE OF CORRECTION

PATENT NO. : 4,510,628
DATED : April 16, 1985
INVENTOR(S) : Willem J. Kolff

It is certified that error appears in the above-identified patent and that said Letters Patent is hereby corrected as shown below:

```
Column 3, line 21, "mole" should be --mold--
Column 3, line 40, "an addition" should be --in addition--
Column 3, line 62, "and ventricles" should be --or ventricles--
Column 4, line 8, "prevent" should be --present--
Column 4, line 23, "ow" should be --or--
Column 5, line 61, "residing" should be --resides--
Column 6, line 9, "artificiial" should be --artificial--
Column 7, line 7, "numberal" should be --numeral--
Column 8, line 48, "permits" should be --permit--

Column 9, line 64, "Artificial" should be --artificial--
```

Signed and Sealed this

Tenth Day of September 1985

[SEAL]

Attest:

DONALD J. QUIGG

Attesting Officer    Acting Commissioner of Patents and Trademarks - Designate